April 17, 1962 G. J. VON ABRAMS Plant Pat. 2,137
ROSE PLANT
Filed Feb. 6, 1961
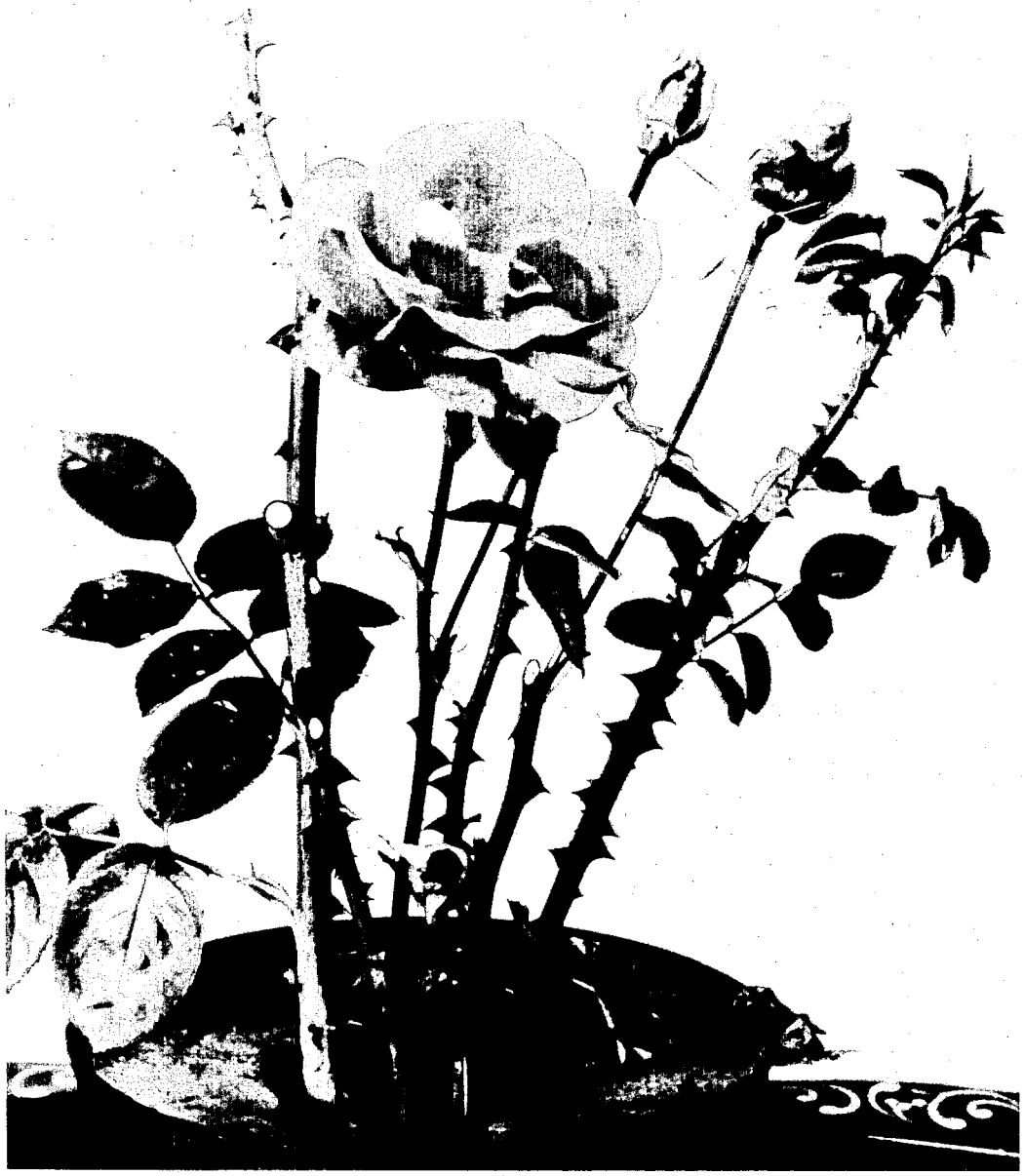
Inventor
Gordon J. Von Abrams
by F. H. Geisler.
Atty.

United States Patent Office

Plant Pat. 2,137
Patented Apr. 17, 1962

2,137
ROSE PLANT

Gordon J. Von Abrams, Portland, Oreg., assignor to Eldon Pinkeney Dering, Scappoose, Oreg.

Filed Feb. 6, 1961, Ser. No. 87,514
1 Claim. (Cl. 47—61)

This invention comprises a new and distinct variety of rose plant of the commercial "Grandiflora" class. The novel and distinguishing characteristics are its tall upright growth habit, with blooms produced on long stems both singly and in relatively large clusters, and the clear dark red color and velvety texture of its well-formed flowers.

This new variety resulted from the pollination by me of the rose variety "Carrousel" (Plant Patent No. 1,066) with the rose variety "Charles Mallerin" (Plant Patent No. 933). The pollinating took plate at Scappoose, Oregon, in the spring of 1953 and the first flower was produced in the spring of 1954. The first asexual propagation was performed in Scappoose, Oregon, in 1955 by bud-grafting, and since then this new rose plant has been found to retain its distinguishing characteristics through successive propagations by bud-grafting.

The plant habit of this rose plant is similar to that of the seed parent "Carrousel," but the new variety tends to be more open, more upright and more vigorous and to have more thorns. The flower color is much darker red, less blue, and the texture of the inner surface of the petals is more velvety than in the case of the "Carrousel." In the bud stage the outer surface of the outside petals of "Carrousel" are strongly pubescent, but this does not hold true for the new variety. In comparison with the rose "Roundelay" this new variety has fewer petals and is more open in form, and the flower color is darker, more velvety red, and more luminescent in appearance. The growth habit and the combination of flower form and flower color, as hereinafter described in more detail, make this new variety quite distinct.

The accompanying illustration shows the plant in color with one full bloom and buds, the illustration being made from a plant in bloom outside in July at Scappoose, Oregon. A detailed description follows in which the following standard references for color are cited:

(1) Wilson, R. F.; Royal Horticultural Society Colour Chart, England, 1940.

(2) Ridgway, R.; Color Standards and Color Nomenclature, Washington, D.C., 1912.

(3) Nickerson Color Fan, Munsell Color Co., Baltimore, 1957.

*Flowers*

The flowers are borne singly on long stems to several per stem on long erect pedicels. The plant blooms abundantly outdoors and blooms nearly continuously during the growing season.

The open flower is medium in size, from about 8 to 10 cm. across. The flower is high centered at first, later in maturity becoming moderately flat. The petals are cupped inwardly at first, gradually rolling loosely outward near the margins. The flower has a light, sweet fragrance.

The deep red color of the flower is not adequately matched by the available color standards of Wilson, Ridgway, or Nickerson. The general color effect (face on) of the newly opened flower is near Cardinal Red (Wilson 822, page 168) with darker shadings and giving the impression of luminescence. The general color effect (face on) of the flower after being open for about three days is darker than Rose Red (Wilson 724, page 158) and appearing luminescent. The flower color is quite stable under most weather conditions, but becomes bluer and less intense under high temperature and high light intensity. The flowers last about five days (on plants grown outside in Scappoose, Oregon) and, when cut from an outdoor plant, last about four days at room temperature. The flower opens well under all but the most severe weather conditions.

Petals:

*Substance.*—Medium hard; slightly stiff; medium thick.

*Texture.*—Outside—satiny. Inside—slightly velvety.

*Shape.*—Outside petal—broad obovate, near orbicular (i.e.—4 cm. long x 4 cm. wide). Apex often irregular, but typically rounded, or lightly retuse, with small protruding tip. There are usually 2 or 3 small contorted outer petals. Inside petal—broad obovate (i.e.—3.3 x 3.5 cm.); apex usually irregular. Petaloids—usually 2 or 3, irregular.

*Flower Color Description in Detail*

The following description of a newly opened flower was made in September, 1959, from a specimen, or specimens, grown outdoors near Scappoose, Oregon.

Outside petal: Outer (dorsal) surface—basal fan very small, near white. General color near Chrysanthemum Crimson (Wilson, 824, p. 169), but darker toward the apex; or between Pomegranate Purple (Ridgway, 71. V–RR. *i*, Plate XII) and Bordeaux (Ridgway, 71. V–RR. *k*, Plate XII). The basal area is somewhat lighter and brighter than the apical area. Irregular near-black areas may occur near apex. Inner surface—basal fan small, near white. The best available comparison is to the Ridgway, 69. RV–R. series, Plate XII, Tyrian Rose thru Violet Carmine. The basal area may be as light as Tyrian Rose (Ridgway, 69. RV–R. Plate XII) or between Tyrian Rose and Rose Red (Ridgway, 71. V–RR. Plate XII), but the general effect is much darker, as dark as Violet Carmine (Ridgway, 69. RV–R. *m*, Plate XII), or darker. This color is complicated by velvety texture, and appears luminescent. Irregular near-black areas may occur toward apex.

Intermediate petal: Outer surface—basal fan very small, near white. Between Cardinal Red (Wilson, 822/1, p. 168) and Chrysanthemum Crimson (Wilson, 824/1, p. 169), nearer the latter. Inner surface—basal fan small, near white. Possibly between Cardinal Red (Wilson, 822, p. 168) and Chrysanthemum Crimson (Wilson, 824, p. 169) but it is darker, and appears luminescent.

Inside petal: As intermediate petal.

The following description of a mature flower was made in September, 1959, from a specimen, or specimens, which had been open for a period of three days on a plant grown outdoors, near Scappoose, Oregon.

Outside petal: Outer surface—basal fan very small; near white. General color related to Chrysanthemum Crimson (Wilson, 824 to 824/3, p. 169). Lighter near base, darker near apex. Irregular areas near black may occur, particularly toward apex, apparently corresponding to the near-black markings in the bud stage. Inner surface—basal fan near white. Related to Rose Red (Wilson, 724, p. 158) and Chrysanthemum Crimson (Wilson, 824, p. 169). Near Rose Red near base, darker above. The general color appears much darker than Rose Red (Wilson, 724) but without the dullness of Chrysanthemum Crimson (Wilson, 824). Appears luminescent. Some, but not all, of the outside petals show near-black markings toward the apex, and these areas are associated with early dessication and cellular degeneration.

Intermediate petal: Outer surface—near Chrysanthemum Crimson (Wilson, 824/3, p. 169). Inner surface— darker than Rose Red (Wilson, 724, p. 158) but appears luminescent. Not as dark as outside petal.

Inside petal: As intermediate petal.

*Flower Bud*

Pedicel:

*Size.*—Long (i.e.—7 cm.); medium caliber (i.e.—3–3.5 mm.).

*Strength.*—Erect to stiff.

*Color.*—Near Scheele's Green (Ridgway, 33. GY–G. *i*, Plate VI) flushed with near Vandyke Red (Ridgway, 1'. RED. *k*, Plate XIII).

*Surface.*—Few to several reddish gland-tipped cilia and prickles; slightly rough.

Sepals: Adnate.

*Size.*—Medium (i.e.—1 x 2.8 cm.).

*Form.*—Spear-shaped.

*Foliaceous appendages.*—Marginal—normally present on one or both edges of 3 of the 5 sepals. Moderate serration, gland-tipped, medium size. Apical—medium-small; lightly serrate at base. Margins—most, but not all, with few gland-tipped cilia. Surface: outer—slightly rough, with few or very few glands; inner—matted white; to mentose. Color: outer surface—near Scheele's Green (Wilson, 860, p. 175) flushed with near Victoria Lake (Ridgway, 1. RED. *m*, Plate I); inner surface—near Clear Fluorite Green (Ridgway, 33". GY–G. *b*, Plate XXXII). Behavior—reflex early, but seldom clasp pedicel.

Before calyx breaks:

*Size.*—Large medium (i.e.—1.8 cm. wide x 2.4 cm. long, excluding receptacle).

*Form.*—Medium pointed. With few foliaceous appendages on surface of bud (on lateral margins of some sepals). With usually slender, lightly serrate, foliaceous parts extending beyond the point of the bud ¼ or less than ¼ its length.

*Color.*—Near between Scheele's Green (Ridgway, 33. GY–G. *i*, Plate VI) and Grass Green (Ridgway, 33. GY–G. *k*, Plate VI), irregularly flushed with near Bordeaux (Ridgway, 71. V–RR. *k*, Plate XII).

As calyx breaks: Exposed petal color—near from Purple Madder (Wilson, 1028, p. 181) to Maroon (Wilson, 1030, p. 185) with near-black markings.

As first petal opens:

*Size of bud.*—Medium.

*Form of bud.*—Oval to flat-topped.

*Color.*—Outer surface—near Ruby Red (Wilson, 827, p. 171), with darker flush, to near black. Inner surface—related to Tyrian Purple (Wilson, 727, p. 159) but much darker. As dark as Purple Madder (Wilson, 1028, p. 181) but not as dull, appearing luminescent and velvety.

*Plant*

Foliage:

*Leaves.*—Compound, 3 to 7, usually 5 leaflets. Moderately abundant. Size medium large.

*Leaflets.*—Shape—ovate, near oval. Apex acuminate. Base rounded. Margin doubly to irregularly serrate. Size—medium large (i.e.—4.5 cm. wide x 7 cm. long). Substance—medium hard; medium thick; slightly stiff. Texture—upper surface smooth, glossy. Color: Mature—upper surface—darker than Spinach Green (Wilson, 0960, p. 187); under surface—near Chromium Green (Ridgway, 31". Y–G. *i*, Plate XXXII). Very young—upper surface—near, or darker than, Hay's Maroon (Ridgway, 1'. RED. *m*, Plate XIII); under surface—near between Vandyke Red (Ridgway, 1'. RED. *k*, Plate XIII) and Hay's Maroon (Ridgway, 1'. RED. *m*, Plate XIII).

*Rachis.*—Caliber—medium to heavy. Upper side—center groove medium deep, smooth. Several glandular cilia on lateral ridges. Under side—near smooth. Few glandular cilia; very few small reddish brown thorns.

*Stipules.*—Size—medium large (i.e.—2.1 mm. x 8 mm.). Points—medium, turned out at about 45°. Margins—irregularly serrate; glandular.

*Disease resistance.*—Moderately susceptible to mildew as determined by field and laboratory observation.

Growth:

*Habit.* — Tall (i.e. — 6'), upright, moderately branched.

*Vigor.*—Very vigorous.

*Canes.*—Moderately heavy.

*Main stems (of current year's growth).*—Caliber—large (i.e.—12 mm.). Color—near Light Hellebore Green (Ridgway, 25' YG–Y. *k*, Plate XVII). When polished, near Parrot Green (Ridgway, 31. Y–G. *k*, Plate VI) or slightly darker. Surface—quite glaucous; few slender corky lesions, Thorns—large (i.e.—12 mm. long); numerous; base—narrow obovate to near oval; large (i.e.—5 mm. wide x 13 mm. long); shape—slightly turned downward to straight; nearly symmetrical, with wide sail-like base rounding smoothly, with long acuminate point; color—near between Hazel and Chestnut Brown (Ridgway, 11'. ORANGE. *k* and *m*, Plate XIV).

*Branches (currently bearing fruit).*—Color—near Bice Green (Ridgway, 29'. GG–Y. *k*, Plate XVII). When polished, near Spinach Green (Wilson, 0960/1, p. 187). Surface—moderately glaucous. Thorns—large (i.e.—to 1 cm. long); several to many; base—narrow obovate; medium to large (i.e.—4 mm. x 12 mm.); shape—nearly straight and symmetrical with broad base and long acuminate point, but on some branches (usually smaller branches) the thorns may be smaller and hooked strongly downward; color—near between Hazel and Chestnut Brown (Ridgway, 11'. ORANGE. *k* and *m*), or more red.

*Thorns.*—Small (i.e.—2 mm.); few to many, some gland-tipped.

*Cilia.*—Gland-tipped, few to very many.

Juvenile stems in rapid growth:

*Color.*—Near Victoria Lake (Ridgway, 1. RED. *m*, Plate I), flushed near Scheele's Green (Ridgway, 33. GY–G. *i*, Plate VI).

*Thorns.*—Large—several, often in pairs, impinging; dark red, hooked downward, medium long (i.e.—8 mm.); base oblanceolate (i.e.—3 x 11 mm.). Small—very few to none. Hairs—very few; short; gland-tipped.

*Reproductive Organs*

Stamens:

*Quantity.*—Many.

*Position.*—Arranged regularly, immediately within the corolla on the outer edge of the calyx-tube disc.

*Filaments.*—Length variable (i.e.—from 2 to 10 mm.); nearly all with anthers. Pale yellow at base, reddish above.

*Anthers.*—Medium size. All mature within a short period of time. Color near Moderate Orange Yellow (Nickerson, 10YR 8/10).

*Pollen.*—Moderately abundant. Viable. Color near Strong Orange Yellow (Nickerson, 7.5YR 7/11) or lighter.

Pistils:

*Quantity.*—Medium number, protruding ca. 1 cm. or less above calyx tube disc, in fairly flat-topped cluster.

*Styles.*—Medium caliber and length. Loosely bunched. Somewhat contorted, but not abnormally. Pale green. Embedded in cottony tissue.

*Stigma.*—Medium small. Pale grayish green.

*Ovaries.*—Enclosed in receptacle. Some irregular exposure.

Receptacle and calyx-tube:

*Size.*—Small-medium (i.e.—1 cm. x 1 cm.).

*Shape.*—Ordinary (short columnar with smoothly rounded base).

*Surface.*—Quite smooth, with very few glandular cilia.

*Color.*—Near Scheele's Green (Wilson, 860/1, p. 175).

Fruit aggregate ("seed pod"):

*Size.*—Medium large (i.e.—2.3 x 2.3 cm.).

*Shape.*—Globular. Often with several seed exposed.

*Surface.*—Smooth.

*Sepals.*—Usually persist.

*Wall.*—Medium thick, fleshy.

*Color.*—Variable, orange at maturity.

Seed: Many; medium large; viable.

Having thus disclosed my invention, I claim:

A new and distinct variety of rose plant of the commercial "Grandiflora" class characterized particularly by its tall upright growth habit, its abundant, well-formed flowers produced both singly and in clusters, and the dark red color and velvety texture of the flowers.

No references cited.